US011987547B2

(12) United States Patent
Pretz et al.

(10) Patent No.: US 11,987,547 B2
(45) Date of Patent: May 21, 2024

(54) METHODS FOR FORMING LIGHT OLEFINS THAT INCLUDE USE OF COOLED PRODUCT AS A RECYCLED QUENCH STREAM

(71) Applicant: Dow Global Technologies LLC, Midland, MI (US)

(72) Inventors: Matthew T. Pretz, Lake Jackson, TX (US); Hangyao Wang, Pearland, TX (US); Anthony Plauck, Pearland, TX (US); Adam M. McNeeley, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 6 days.

(21) Appl. No.: 17/622,412

(22) PCT Filed: Jun. 12, 2020

(86) PCT No.: PCT/US2020/037420
§ 371 (c)(1),
(2) Date: Dec. 23, 2021

(87) PCT Pub. No.: WO2020/263599
PCT Pub. Date: Dec. 30, 2020

(65) Prior Publication Data
US 2022/0356130 A1    Nov. 10, 2022

Related U.S. Application Data

(60) Provisional application No. 62/868,340, filed on Jun. 28, 2019.

(51) Int. Cl.
*C07C 5/333* (2006.01)

(52) U.S. Cl.
CPC ........ *C07C 5/3337* (2013.01); *C07C 2523/08* (2013.01); *C07C 2523/42* (2013.01); *C07C 2523/62* (2013.01)

(58) Field of Classification Search
CPC ..... C07C 5/333; C07C 5/3335; C07C 5/3337; C07C 2523/08; C07C 2523/42;
(Continued)

(56) References Cited

U.S. PATENT DOCUMENTS 2,889,383 A    6/1959  Green
4,579,716 A    4/1986  Krambeck et al.
(Continued)

FOREIGN PATENT DOCUMENTS

WO    2005/077867 A3    8/2005
WO    2018/236630 A2    12/2018

OTHER PUBLICATIONS

Bartlit, Kinetics of Ethane Pyrolysis, A.I.CH.E. Journal, 1965, pp. 562-472, vol. 11 No 3.
(Continued)

*Primary Examiner* — In Suk C Bullock
*Assistant Examiner* — Jason Y Chong
(74) *Attorney, Agent, or Firm* — Dinsmore & Shohl LLP

(57) ABSTRACT

According to one or more embodiments, a method for forming light olefins may comprise introducing a hydrocarbon feed stream into a reactor, reacting the hydrocarbon feed stream with a dehydrogenation catalyst in the reactor to form a high temperature dehydrogenated product, separating at least a portion of the dehydrogenation catalyst from the high temperature dehydrogenated product in a primary separation device, combining the high temperature dehydrogenation product with a quench stream to cool the high temperature dehydrogenation product and form an intermediate temperature dehydrogenation product, and cooling the intermediate (Continued)

temperature dehydrogenation product to form a cooled dehydrogenation product.

19 Claims, 9 Drawing Sheets

(58) Field of Classification Search
CPC ....... C07C 2523/62; C07C 7/00; C07C 11/04; C07C 11/06
See application file for complete search history.

(56) References Cited

U.S. PATENT DOCUMENTS

| | | | |
|---|---|---|---|
| 5,043,058 A | | 8/1991 | Forgac et al. |
| 5,190,650 A | | 3/1993 | Tammera et al. |
| 5,220,093 A | * | 6/1993 | Gartside ................. C07C 5/333 |
| | | | 585/654 |
| 5,275,641 A | | 1/1994 | Tammera et al. |
| 5,288,920 A | | 2/1994 | Chan et al. |
| 5,662,868 A | | 9/1997 | Letzsch et al. |
| 8,669,406 B2 | | 3/2014 | Pretz et al. |
| 8,921,627 B2 | | 12/2014 | Sechrist et al. |
| 2004/0025535 A1 | * | 2/2004 | Mak ....................... F25J 3/0209 |
| | | | 62/929 |
| 2011/0319692 A1 | * | 12/2011 | Spieker ................... C07C 5/333 |
| | | | 585/659 |
| 2016/0272559 A1 | * | 9/2016 | Pretz ..................... C07C 5/3337 |
| 2020/0197891 A1 | | 6/2020 | Pretz |
| 2020/0299212 A1 | * | 9/2020 | Tallman ................. C10G 55/06 |

OTHER PUBLICATIONS

Buekens, Thermal Cracking of Propane, I&EC Process Design and Development, 1968, pp. 435-447, vol. 7 No. 3.
Domke, Investigation of the Kinetics of Ethylbenzene Pyrolysis Using a Temperature-Scanning Reactor, American Chemical Society, 2001, pp. 5878-5884, vol. 40, No. 25.
Sagert, Kinetics and Mechanisms of the Pyrolysis of n-Butane, Canadian Journal of Chemistry, 1963, pp. 838-847, vol. 41.
International Preliminary Report on Patentability International Patent Application No. PCT/US2020/037420 dated Dec. 4, 2020 (7 total pages).
Communication pursuant to Rules 161 (1) and 162 for EP Application No. 20735746.8, dated Feb. 8, 2022, (3 total pages).
International Search Report and Written Opinion issued by the European Patent Office acting as International Searching Authority for International Patent Application No. PCT/US2020/037420 dated Dec. 4, 2020 (13 total pages).
Singapore Written Opinion and Search Report dated Sep. 10, 2023, SG Patent Application No. 11202113940Q, 10 pgs.
Chinese Office Action dated Nov. 7, 2023, pertaining to CN Patent Application No. 202080046937.6, 24 pgs.
Chinese Office Action dated Feb. 8, 2024, pertaining to CN Patent Application No. 202080046937.6, 24 pgs.

* cited by examiner

METHODS FOR FORMING LIGHT OLEFINS THAT INCLUDE USE OF COOLED PRODUCT AS A RECYCLED QUENCH STREAM

CROSS-REFERENCE TO RELATED APPLICATIONS

This application is a National Stage Entry under 35 U.S.C. § 371 of International Patent Application No. PCT/US2020/037420, filed Jun. 12, 2020, which claims priority to U.S. Provisional Patent Application No. 62/868,340, filed on Jun. 28, 2019, the entire disclosures of both of which are hereby incorporated by reference.

BACKGROUND

Field

The present disclosure generally relates to chemical processing systems and, more specifically, to dehydrogenation chemical processing systems.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene. Light olefins may be produced by different reaction processes depending on the given chemical feed stream, which may be a product stream from a crude oil refining operation. Many light olefins may be produced through catalytic processes, such as catalytic dehydrogenation, in which the feed stream is contacted with a fluidized catalyst that facilitates conversion of the feed stream into the light olefins. In such systems, reaction selectivity for the light olefins may be important to overall process efficiency.

BRIEF SUMMARY

There is a continued need for improved systems and methods for producing light olefins. It has been observed that elevated temperatures of dehydrogenation product streams may lead to undesired thermal cracking of the product stream, which may reduce the system selectivity for the desired light olefins. For example, unreacted alkanes and/or desired product olefins in the product stream may thermally crack in the catalyst separation portions and other downstream portions of reactor systems prior to the product stream being cooled by, for example, a heat exchanger. To mitigate or wholly correct this phenomenon, systems disclosed herein recycle a portion of the product stream once it has been cooled by, for example, a heat exchanger. The recycle stream (i.e., quench stream) of cooled product reduces the temperature of the high temperature product stream to an intermediate temperature which has a reduced rate of undesirable thermal cracking. For example, in some reaction systems disclosed herein, a cooled product stream is recycled to contact the high temperature product stream shortly after the product stream exits the primary separation device that separates most of the solid catalyst from the product stream gas. Examples of solid/gas separation devices suitable for use herein include, without limitation, a cyclonic separation device (i.e., a cyclone), a filter, or any other device suitable for separating gases from solids. Contact by such a quench stream cools the product stream to an intermediate temperature that has a reduced thermal cracking rate as compared to the product stream prior to contact with the quench stream. As such, thermal cracking is reduced at least from the point where the recycle stream (i.e., quench stream) contacts the high temperature product stream to the point where the product stream is cooled by, for example, a heat exchanger.

According to one or more embodiments, a method for forming light olefins may comprise introducing a hydrocarbon feed stream into a reactor, reacting the hydrocarbon feed stream with a dehydrogenation catalyst in the reactor to form a high temperature dehydrogenated product, the dehydrogenated product comprising at least a portion of the hydrocarbon feed stream that was not catalytically reacted, separating at least a portion of the dehydrogenation catalyst from the high temperature dehydrogenated product in a primary separation device, wherein the temperature of the dehydrogenated product and dehydrogenation catalyst in the primary separation device is at least 550° C. The method may further comprise, following the exit of high temperature dehydrogenation product from the primary separation device, combining the high temperature dehydrogenation product with a quench stream to cool the high temperature dehydrogenation product and form an intermediate temperature dehydrogenation product, wherein the quench stream is a gas stream, and wherein temperature of the intermediate temperature dehydrogenation product is at least 10° C. less than the temperature of the high temperature dehydrogenation product. The method may further comprise cooling the intermediate temperature dehydrogenation product to form a cooled dehydrogenation product, wherein a portion of the cooled dehydrogenation product is utilized as at least a portion of the quench stream.

According to one or more additional embodiments, a method for forming light olefins may comprise introducing a hydrocarbon feed stream into a reactor, reacting the hydrocarbon feed stream with a dehydrogenation catalyst in the reactor to form a high temperature dehydrogenated product, the dehydrogenated product comprising at least a portion of the hydrocarbon feed stream that was not catalytically reacted, and separating at least a portion of the dehydrogenation catalyst from the high temperature dehydrogenated product in a primary separation device, wherein the temperature of the dehydrogenated product and dehydrogenation catalyst in the primary separation device is at least 550° C. The method may further comprise, following the exit of high temperature dehydrogenation product from the primary separation device, combining the high temperature dehydrogenation product with a quench stream to cool the high temperature dehydrogenation product and form an intermediate temperature dehydrogenation product, wherein the quench stream is a gas stream, and wherein temperature of the intermediate temperature dehydrogenation product is at least 10° C. less than the temperature of the high temperature dehydrogenation product. The method may further comprise passing the intermediate temperature product to a secondary separation device, where the remainder of the dehydrogenation catalyst is removed from the intermediate temperature product, and cooling the intermediate temperature dehydrogenation product to form a cooled dehydrogenation product, wherein a portion of the cooled dehydrogenation product is utilized as at least a portion of the quench stream.

It is to be understood that both the foregoing brief summary and the following detailed description present embodiments of the technology, and are intended to provide an overview or framework for understanding the nature and character of the technology as it is claimed. The accompanying drawings are included to provide a further understanding of the technology, and are incorporated into and constitute a part of this specification. The drawings illustrate various embodiments and, together with the description, serve to explain the principles and operations of the technology. Additionally, the drawings and descriptions are meant to be merely illustrative, and are not intended to limit the scope of the claims in any manner.

Additional features and advantages of the technology disclosed herein will be set forth in the detailed description which follows, and in part will be readily apparent to those skilled in the art from that description or recognized by practicing the technology as described herein, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
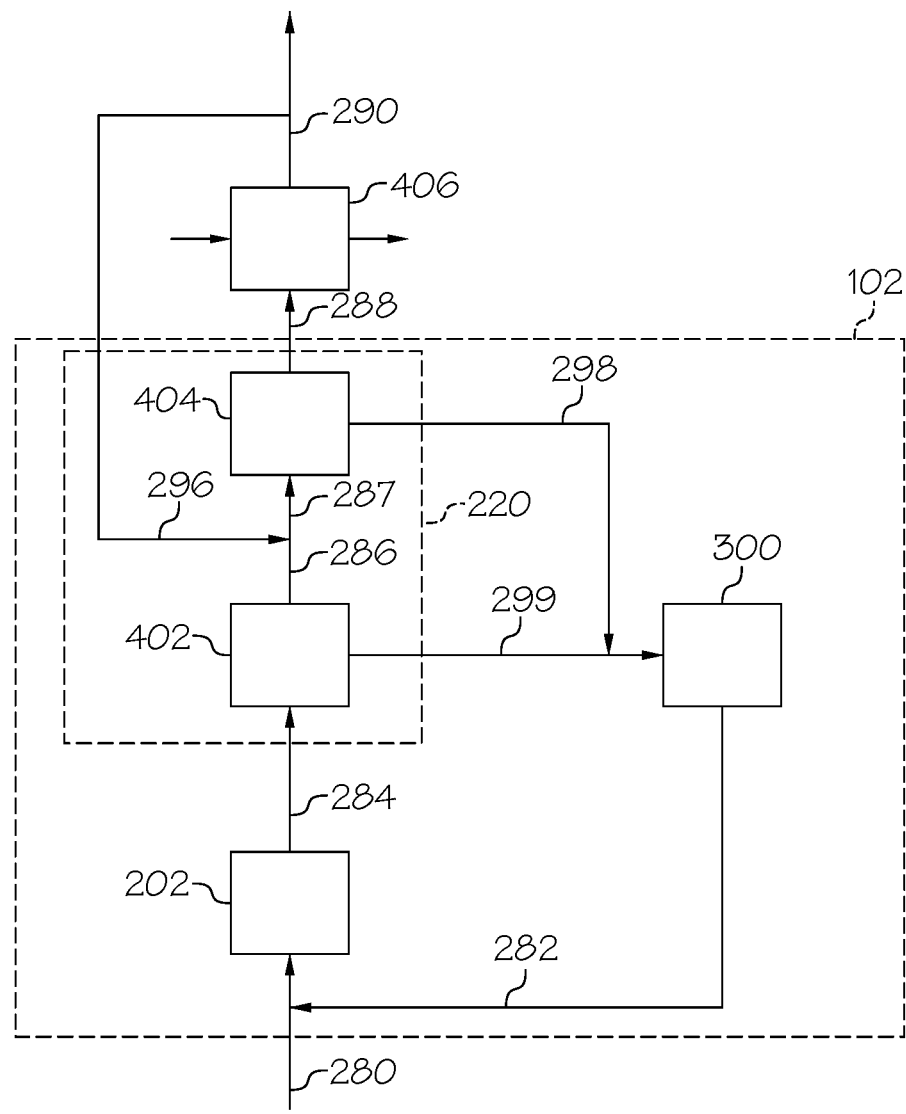
FIG. 1 depicts a generalized flow diagram of a reactor system having downstream cooling and a recycled quench stream, according to one or more embodiments described herein.

It should be understood that the drawings are schematic in nature, and do not include some components of a reactor system commonly employed in the art, such as, without limitation, temperature transmitters, pressure transmitters, flow meters, pumps, valves, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the presently disclosed technology are described with respect to the several figures. FIG. 1 depicts an example flow diagram representing a reactor system according to one or more embodiments presently disclosed. It is noted that many process and equipment details of one or more embodiments of the system of FIG. 1 are described herein with reference to FIGS. 2-4. It will be appreciated, in view of the other figures, that one or more components of FIG. 1 may be integral or adjacent with one another and some streams may be only representations depicting material movement and a physical pipe or other means of transport may not be physically present (e.g., the stream passes directly from a reactor to a separator that are adjacent one another).

Still referring to FIG. 1, the reactor system 102 may include a reactor 202, a separation device 220, and a catalyst processing portion 300. Generally, the main reaction, such as a dehydrogenation reaction, takes place in the reactor 202, where reactant stream 280 (sometimes referred to herein as a hydrocarbon feed stream) from outside of the depicted system is combined with regenerated catalyst of stream 282 from the catalyst processing portion and passed into the reactor 202. Following the reaction, the catalyst, unreacted chemicals, and product chemicals are transferred via stream 284 to the separation device 220. It should be understood that a "product stream" may include both reaction products and unreacted components from reactant stream 280. Reactant stream 280 may comprise one or more of propane, n-butane, iso-butane, ethane, or ethylbenzene.

Stream 284 is referred to sometimes herein as a high temperature dehydrogenated product. Generally, stream 284 has a temperature near that of of equal to the temperature in the reactor 202. The temperature may depend upon the reaction and utilized catalyst system. In one or more embodiments, stream 284 has a temperature of at least 550° C. (such as at least 575° C., at least 600° C., at least 625° C., at least 650° C., at least 675° C., at least 700° C., or even at least 725° C.). For example, when propane is dehydrogenated, the temperature of stream 284 may be approximately 620° C. (such as from 600° C. to 640° C.). When ethylbenzene is dehydrogenated, the temperature of stream 284 may be approximately 595° C. (such as from 575° C. to 615° C.). When ethane is dehydrogenated, the temperature of stream 284 may be approximately 750° C. (such as from 730° C. to 770° C.). When butane is dehydrogenated, the temperature of stream 284 may be approximately 600° C. (such as from 580° C. to 620° C.).

The separation device 220 may include a primary separation device 402 and a secondary separation device 404. However, it should be understood that the secondary separation device 404 is not present in some embodiments. In additional embodiments, the primary separation device 402 and/or secondary separation device 404 may be, without limitation, cyclones, filters, or other suitable devices for separating solids, such as catalyst, from gases. Following the separation of at least a portion (usually the majority) of the catalyst of stream 284 from the gas phase reactant and product chemicals in the primary separation device 402, the catalyst is passed via stream 299 to the catalyst processing portion 300 and the product and reactant gases (still sometimes referred to as a high temperature dehydrogenated product) may be passed out of the primary separation device 402 via stream 286. The temperature of stream 286 may be about equivalent to that of stream 284.

In one or more embodiments, following the exit of high temperature dehydrogenation product via stream 286 from the primary separation device, the high temperature dehydrogenation product may be combined with a quench stream 296 to cool the high temperature dehydrogenation product and form stream 287 (sometimes referred to as the intermediate temperature dehydrogenation product). The quench stream may be a gas stream that is a downstream portion of stream 286, which is explained in detail herein. The quench stream may include one or more of ethylene, propylene, or a butene isomer (e.g., the reaction products).

The quench stream 296 may have a temperature substantially below that of stream 286. For example, the quench stream 296 may have a temperature of less than 150° C., such as less than 125° C., less than 100° C., less than 75° C., or even less than 50° C. The quench stream 296 may be approximately the same temperature as stream 290, the outlet of the heat exchanger 406. In one or more embodiments, the temperature of the quench stream 296 may be at least 200° C. less than the temperature of stream 286 (such as at least 250° C. less, at least 300° C. less, at least 350° C. less, at least 400° C. less, at least 450° C. less, or even at least 500° C. less than the temperature of stream 286).

The mixing of the quench stream 296 with stream 286 forms intermediate temperature dehydrogenation product in stream 287. The temperature of stream 287 may be at least 10° C. less than stream 286. For example, the temperature of stream 287 may be at least 15° C., 20° C., 25° C., 30° C., 35° C., 40° C., 45° C., 50° C., 60° C., 70° C., 80° C., 90° C., 100° C., 110° C., 120° C., 130° C., 140° C., or even 150° C. less than stream 286. The rate of thermal cracking of one or more of propane, n-butane, ethane, or ethylbenzene, and reaction products thereof, may be reduced in stream 287 as compared with stream 286. For example, the rate of thermal cracking of these components in stream 287, due at least in part to the reduction in temperature, may be less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or even less than 5% of that in stream 286.

The secondary separation device 404 may further separate any remaining solids such as catalyst in stream 287 and return them to the catalyst processing portion 300 via line 298. Stream 288 may contain little or no solids. Stream 288 may be still referred to as an intermediate temperature dehydrogenation product since it is about the same temperature as stream 287. Stream 288 is then processed to cool its contents via, for example, heat exchanger 406. In additional embodiments, the cooling may be performed by a liquid quenching system or other known means of cooling a stream. The product stream of the heat exchanger 406 is stream 290, which may be referred to as a cooled dehydrogenation product. The temperature of stream 290 may be about the same as that described with respect to the quench stream 296. It should be understood that stream 290 and or stream 296 may be subjected to compression such that they flow in the desired direction. For example, stream 296 may generally have a greater pressure than that of stream 287 for transport purposes.

To form the quench stream 296, at least a portion of stream 290 is recycled back into the system. It should be noted that the chemical contents of stream 296 may be similar or identical to those of stream 286 (i.e., no further reactions outside of some residual thermal cracking have taken place since those in reactor 20). The quenching of stream 286 by contact with the quench stream 296 may cool the contents of stream 286 to a temperature which substantially reduces the reaction rate of thermal cracking. Stream 286 may be at a temperature where thermal cracking occurs and such thermal cracking may reduce selectivity of the desired reaction products.

It should be understood that the quench stream does not include steam in any substantial amount. For example, the quench stream comprises less than 3 wt. % steam (such as less than 2 wt. % steam, less than 1 wt. % steam, or substantially no steam in additional embodiments). As is described in the examples which follow, the use of a dehydrogenation product stream as the quench may have numerous benefits as compared to the use of steam.

Figure 2:
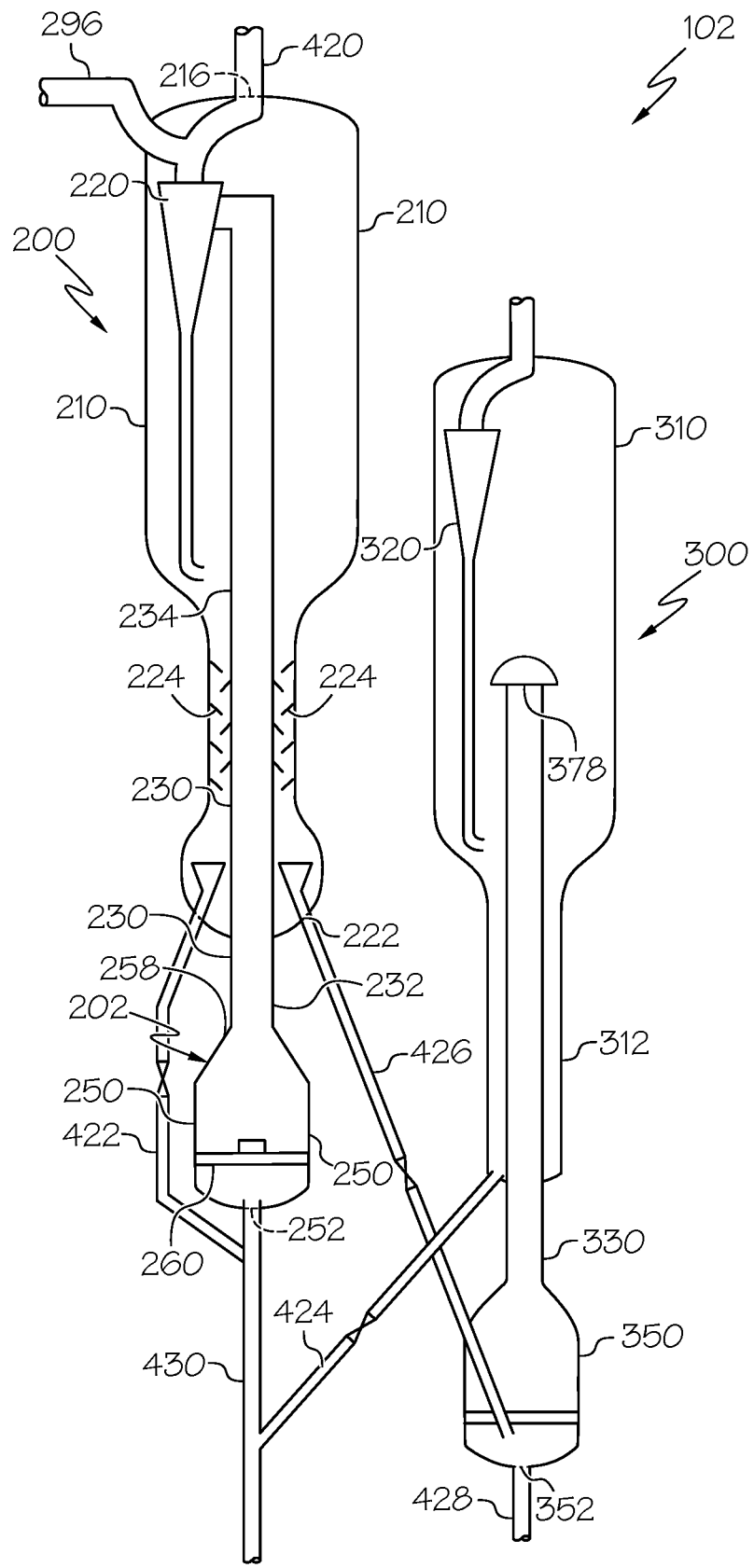
FIG. 2 schematically depicts a portion of a reactor system, according to one or more embodiments described herein.

An example reactor system and methods for processing the chemical streams according to use of such a reactor system will now be discussed in detail in view of FIG. 2. While in some cases like numbers are utilized in FIG. 2 with respect to FIG. 1, it should be understood that the embodiments of FIG. 1 may utilize a wide variety of reactor types and that of FIG. 2 is only an example of one such type. It should be understood that the quenching embodiments described herein may be suitable for use with other reactor system configurations, including those that do not include regeneration by cyclical catalyst movement as described herein.

Now referring to FIG. 2, an example reactor system 102 is schematically depicted. The reactor system 102 generally comprises multiple system components, such as a reactor portion 200 and a catalyst processing portion 300. As used herein in the context of FIG. 2, the reactor portion 200 generally refers to the portion of a reactor system 102 in which the major process reaction takes place. For example, the reactor system 102 may be a dehydrogenation system in which the feed stream is dehydrogenated in the presence of the dehydrogenation catalyst in the reactor portion 200 of the reactor system 102.

The reactor portion 200 comprises a reactor 202 which may include a downstream reactor section 230 and an upstream reactor section 250. According to one or more embodiments, as depicted in FIG. 2, the reactor portion 200 may additionally include a catalyst separation section 210 which serves to separate the catalyst from the chemical products formed in the reactor 202. Also, as used herein, the catalyst processing portion 300 generally refers to the portion of a reactor system 102 in which the catalyst is in some way processed, such as by combustion. The catalyst processing portion 300 may comprise a combustor 350 and a riser 330, and may optionally comprise a catalyst separation section 310. In some embodiments, the catalyst may be regenerated by burning off contaminants like coke in the catalyst processing portion 300. In additional embodiments, the catalyst may be heated in the catalyst processing portion 300. A supplemental fuel may be utilized to heat the catalyst in the catalyst processing portion 300 if coke or another combustible material is not formed on the catalyst, or an amount of coke formed on the catalyst is not sufficient to burn off to heat the catalyst to a desired temperature. In one or more embodiments, the catalyst separation section 210 may be in fluid communication with the combustor 350 (e.g., via standpipe 426) and the catalyst separation section 310 may be in fluid communication with the upstream reactor section 250 (e.g., via standpipe 424 and transport riser 430).

As described with respect to FIG. 2, the feed stream may enter the transport riser 430, and the product stream may exit the reactor system 102 via pipe 420. According to one or more embodiments, the reactor system 102 may be operated by feeding a chemical feed (e.g., in a feed stream) and a fluidized catalyst into the upstream reactor section 250. The chemical feed contacts the catalyst in the upstream reactor section 250, and each flow upwardly into and through the downstream reactor section 230 to produce a chemical product. The chemical product and the catalyst may be passed out of the downstream reactor section 230 to a separation device 220 in the catalyst separation section 210. The catalyst is separated from the chemical product in the separation device 220. The chemical product is transported out of the catalyst separation section 210. The separated catalyst is passed from the catalyst separation section 210 to the combustor 350. In the combustor 350, the catalyst may be processed by, for example, combustion. For example, and without limitation, the catalyst may be de-coked and/or supplemental fuel may be combusted to heat the catalyst. The catalyst is then passed out of the combustor 350 and through the riser 330 to a riser termination separator 378, where the gas and solid components from the riser 330 are at least partially separated. The vapor and remaining solids are transported to a secondary separation device 320 in the catalyst separation section 310 where the remaining catalyst is separated from the gases from the catalyst processing (e.g., gases emitted by combustion of spent catalyst or supplemental fuel). The separated catalyst is then passed from the catalyst separation section 310 to the upstream reactor section 250 via standpipe 424 and transport riser 430, where it is further utilized in a catalytic reaction. Thus, the catalyst, in operation, may cycle between the reactor portion 200 and the catalyst processing portion 300. In general, the processed chemical streams, including the feed streams and product streams may be gaseous, and the catalyst may be fluidized particulate solid.

As depicted in FIG. 2, the upstream reactor section 250 may be positioned below the downstream reactor section 230. Such a configuration may be referred to as an upflow configuration in the reactor 202. The reactor 202 may also be a downflow reactor in which the upstream reactor section 250 may be position above the downstream reactor section 230. Other reactor configurations are also contemplated for the reactor portion 200 of the reactor system 102.

As described herein, the upstream reactor section 250 may include a vessel, drum, barrel, vat, or other container suitable for a given chemical reaction. In one or more embodiments, the upstream reactor section 250 may be generally cylindrical in shape (i.e., having a substantially circular cross-sectional shape), or may alternately be non-cylindrically shaped, such as prism shaped with cross-sectional shapes of triangles, rectangles, pentagons, hexagons, octagons, ovals, or other polygons or curved closed shapes, or combinations thereof. The upstream reactor section 250, as used throughout this disclosure, may generally include a metallic frame, and may additionally include refractory linings or other materials utilized to protect the metallic frame and/or control process conditions. As depicted in FIG. 2, the upstream reactor section 250 may include a lower reactor portion catalyst inlet port 252 defining the connection of transport riser 430 to the upstream reactor section 250.

The upstream reactor section 250 may be connected to a transport riser 430 which, in operation, may provide processed catalyst and/or reactant chemicals in a feed stream to the reactor portion 200. The processed catalyst and/or reactant chemicals may be mixed with a distributor 260 housed in the upstream reactor section 250. The catalyst entering the upstream reactor section 250 via transport riser 430 may be passed through standpipe 424 to a transport riser 430, thus arriving from the catalyst processing portion 300. In some embodiments, catalyst may come directly from the catalyst separation section 210 via standpipe 422 and into a transport riser 430, where it enters the upstream reactor section 250. The catalyst can also be fed via 422 directly to the upstream reactor section 250. This catalyst may be slightly deactivated, but may still, in some embodiments, be suitable for reaction in the upstream reactor section 250. As used herein, "deactivated" may refer to a catalyst which is contaminated with a substance such as coke, or is cooler in temperature than desired. Regeneration may remove the contaminant such as coke, raise the temperature of the catalyst, or both.

Still referring to FIG. 2, the reactor portion 200 may comprise a downstream reactor section 230 which acts to transport reactants, products, and/or catalyst from the upstream reactor section 250 to the catalyst separation section 210. In one or more embodiments, the downstream reactor section 230 may be generally cylindrical in shape (i.e., having a substantially circular cross-sectional shape), or may alternately be non-cylindrically shaped, such as prism shaped with cross-sectional shape of triangles, rectangles, pentagons, hexagons, octagons, ovals, or other polygons or curved closed shapes, or combinations thereof. The downstream reactor section 230, as used throughout this disclosure, may generally include a metallic frame, and may additionally include refractory linings or other materials utilized to protect the metallic frame and/or control process conditions.

According to some embodiments, the downstream reactor section 230 may include an external riser section 232 and an internal riser section 234. As used herein, an "external riser section" refers to the portion of the riser that is outside of the catalyst separation section 210, and an "internal riser section" refers to the portion of the riser that is within the catalyst separation section 210. For example, in the embodiment depicted in FIG. 2, the internal riser section 234 of the reactor portion 200 may be positioned within the catalyst separation section 210, while the external riser section 232 is positioned outside of the catalyst separation section 210.

As depicted in FIG. 2, the upstream reactor section 250 may be connected to the downstream reactor section 230 via the transition section 258. The upstream reactor section 250 may generally comprise a greater cross-sectional area than the downstream reactor section 230. The transition section 258 may be tapered from the size of the cross-section of the upstream reactor section 250 to the size of the cross-section of the downstream reactor section 230 such that the transition section 258 projects inwardly from the upstream reactor section 250 to the downstream reactor section 230.

In some embodiments, such as those in which the upstream reactor section 250 and the downstream reactor section 230 have similar cross-sectional shapes, the transition section 258 may be shaped as a frustum. For example, for an embodiment of a reactor portion 200 comprising a cylindrical upstream reactor section 250 and cylindrical downstream reactor section 230, the transition section 258 may be shaped as a conical frustum. However, it should be understood that a wide variety of upstream reactor section 250 shapes are contemplated herein which connect various shapes and sizes of upstream reactor section 250 and downstream reactor section 230.

In one or more embodiments, based on the shape, size, and other processing conditions such as temperature and pressure in the upstream reactor section 250 and the downstream reactor section 230, the upstream reactor section 250 may operate in a manner that is or approaches isothermal, such as in a fast fluidized, turbulent, or bubbling bed upflow reactor, while the downstream reactor section 230 may operate in more of a plug flow manner, such as in a riser reactor. For example, the reactor 202 of FIG. 2 may comprise an upstream reactor section 250 operating as a fast fluidized, turbulent, or bubbling bed reactor and a downstream reactor section 230 operating as a dilute phase riser reactor, with the result that the average catalyst and gas flow moves concurrently upward. As the term is used herein, "average flow" refers to the net flow, i.e., the total upward flow minus the retrograde or reverse flow, as is typical of the behavior of fluidized particles in general. As described herein, a "fast fluidized" reactor may refer to a reactor utilizing a fluidization regime wherein the superficial velocity of the gas phase is greater than the choking velocity and may be semi-dense in operation. As described herein, a "turbulent" reactor may refer to a fluidization regime wherein the superficial velocity of less than the choking velocity and is more dense than the fast fluidized regime. As described herein, a "bubbling bed" reactor may refer to a fluidization regime wherein well defined bubbles in a highly dense bed are present in two distinct phases. The "choking velocity" refers to the minimum velocity required to maintain solids in the dilute-phase mode in a vertical conveying line. As described herein, a "dilute phase riser" may refer to a riser reactor operating at transport velocity, wherein the gas and catalyst have about the same velocity in a dilute phase.

In one or more embodiments, the pressure in the reactor 202 may range from 6.0 to 44.7 pounds per square inch absolute (psia, from about 41.4 kilopascals, kPa, to about 308.2 kPa), but in some embodiments, a narrower selected range, such as from 15.0 psia to 35.0 psia, (from about 103.4 kPa to about 241.3 kPa), may be employed. For example, the pressure may be from 15.0 psia to 30.0 psia (from about 103.4 kPa to about 206.8 kPa), from 17.0 psia to 28.0 psia (from about 117.2 kPa to about 193.1 kPa), or from 19.0 psia to 25.0 psia (from about 131.0 kPa to about 172.4 kPa). Unit conversions from standard (non-SI) to metric (SI) expressions herein include "about" to indicate rounding that may be present in the metric (SI) expressions as a result of conversions.

In additional embodiments, the weight hourly space velocity (WHSV) for the disclosed process may range from 0.1 pound (lb) to 100 lb of chemical feed per hour (h) per lb of catalyst in the reactor (lb feed/h/lb catalyst). For example, where the reactor 202 comprises an upstream reactor section 250 that operates as a fast fluidized, turbulent, or bubbling bed reactor and a downstream reactor section 230 that operates as a dilute phase riser reactor, the superficial gas velocity may range therein from 2 ft/s (about 0.61 m/s) to 10 ft/s (about 3.05 m/s) in the upstream reactor section 250, and from 30 ft/s (about 9.14 m/s) to 70 ft/s (about 21.31 m/s) in the downstream reactor section 230. In additional embodiments, a reactor configuration that is fully of a riser-type may operate at a single high superficial gas velocity, for example, in some embodiments at least 30 ft/s (approximately 9.15 m/s) throughout.

In additional embodiments, the ratio of catalyst to feed stream in the reactor 202 may range from 5 to 100 on a weight to weight (w/w) basis. In some embodiments, the ratio may range from 10 to 40, such as from 12 to 36, or from 12 to 24.

In additional embodiments, the catalyst flux may be from 1 pound per square foot-second (lb/ft$^2$-s) (about 4.89 kg/m$^2$-s) to 20 lb/ft$^2$-s (to about 97.7 kg/m$^2$-s) in the upstream reactor section 250, and from 10 lb/ft$^2$-s (about 48.9 kg/m$^2$-s) to 100 lb/ft$^2$-s (about 489 kg/m$^2$-s) in the downstream reactor section 230.

Still referring to FIG. 2, in operation, the catalyst may move upward through the downstream reactor section 230 (from the upstream reactor section 250), and into the separation device 220. The separated vapors may be removed from the reactor system 102 via a pipe 420 at a gas outlet port 216 of the catalyst separation section 210. According to one or more embodiments, the separation device 220 may comprise one or more separation units, referred to herein as primary and secondary separation units, which may be two or more stages of cyclonic separation. It should be appreciated that FIG. 2 schematically depicts a single cyclone as a generic separation device 220. However, as depicted in FIG. 1, several separation devices, such as cyclones or filters, in series, may be utilized. In embodiments where the separation device 220 comprises more than one separation device, the first separation device into which the fluidized stream enters is referred to a primary separation device. The fluidized effluent from the primary separation device may enter into a secondary separation device for further separation. Primary separation devices may include, for example, primary cyclones, and systems commercially available under the names VSS (commercially available from UOP), LD2 (commercially available from Stone and Webster), and RS2 (commercially available from Stone and Webster). Primary separation devices are described, for example, in U.S. Pat. Nos. 4,579,716; 5,190,650; and 5,275,641, which are each incorporated by reference in their entirety herein. In some separation systems utilizing primary cyclones as the primary cyclonic separation device, one or more set of additional separation devices (i.e., secondary separation devices and/or tertiary separation devices), may be utilized for further separation of the catalyst from the product gas. It should be understood that any primary separation device and/or secondary separation device, in any combination, may be used in embodiments of the invention.

Still referring to FIG. 2, quench stream 296 may contact the gas effluent of the primary separation device and form the intermediate temperature dehydrogenation product. The contents of the quench stream 296 are shown and described above with reference to FIG. 1.

According to some embodiments, following separation from vapors in the separation device 220, the catalyst may generally move through the stripper 224 to the reactor catalyst outlet port 222 where the catalyst is transferred out of the reactor portion 200 via standpipe 426 and into the catalyst processing portion 300. Optionally, the catalyst may also be transferred directly back into the upstream reactor section 250 via standpipe 422. Alternatively, the catalyst may be premixed with processed catalyst in the transport riser 430.

As is described in detail in accordance with the embodiment of FIG. 2, according to one or more embodiments, the catalyst may be processed by one or more of the steps of passing the catalyst from the reactor 202 to the combustor 350, burning a supplemental fuel source or coke from the deactivated catalyst in the combustor 350, and passing the heated catalyst from the combustor 350 to the reactor 202.

Referring now to the catalyst processing portion 300, as depicted in FIG. 2, the combustor 350 of the catalyst processing portion 300 may include one or more lower reactor portion inlet ports 352 and may be in fluid communication with the riser 330. The combustor 350 may be in fluid communication with the catalyst separation section 210 via standpipe 426, which may supply spent catalyst from the reactor portion 200 to the catalyst processing portion 300 for regeneration. The combustor 350 may include an additional lower reactor section inlet port 352 where air inlet 428 connects to the combustor 350. The air inlet 428 may supply reactive gases which may react with the spent catalyst or a supplemental fuel to at least partially regenerate the catalyst. For example, the catalyst may be coked following the reactions in the upstream reactor section 250, and the coke may be removed from the catalyst (i.e., regenerating the catalyst) by a combustion reaction. For example, oxidizer (such as air) may be fed into the combustor 350 via the air inlet 428. Alternatively or additionally, such as when a substantial amount of coke is not formed on the catalyst, a supplemental fuel may be injected into the combustor 350, which may be burned to heat the catalyst. Following combustion, the processed catalyst may be separated in the catalyst separation section 310 and delivered back into the reactor portion 200 via standpipe 424.

According to one or more embodiments, the reaction may be a dehydrogenation reaction. According to such embodiments, the feed stream may comprise one or more of ethane, propane, n-butane, i-butane, or ethylbenzene. For example, if the reaction is a dehydrogenation reaction, then the feed stream may comprise one or more of ethane, propane, n-butane, i-butane, or ethylbenzene. According to one or more embodiments, the feed stream may comprise at least 50 wt. %, at least 60 wt. %, at least 70 wt. %, at least 80 wt. %, at least 90 wt. %, at least 95 wt. % or even at least 99 wt. % of ethane. In additional embodiments, the feed stream may comprise at least 50 wt. %, at least 60 wt. %, at least 70 wt. %, at least 80 wt. %, at least 90 wt. %, at least 95 wt. % or even at least 99 wt. % of propane. In additional embodiments, the feed stream may comprise at least 50 wt. %, at least 60 wt. %, at least 70 wt. %, at least 80 wt. %, at least 90 wt. %, at least 95 wt. % or even at least 99 wt. % of n-butane or i-butane. In additional embodiments, the feed stream may comprise at least 50 wt. %, at least 60 wt. %, at least 70 wt. %, at least 80 wt. %, at least 90 wt. %, at least 95 wt. % or even at least 99 wt. % of i-butane. In additional embodiments, the feed stream may comprise at least 50 wt. %, at least 60 wt. %, at least 70 wt. %, at least 80 wt. %, at least 90 wt. %, at least 95 wt. % or even at least 99 wt. % of the sum of ethylbenzene, ethane, propane, n-butane, and i-butane.

In one or more embodiments, a dehydrogenation reaction may utilize gallium and/or platinum catalyst as a catalyst. In such embodiments, the catalyst may comprise a gallium and/or platinum catalyst. For example, if the reaction is a dehydrogenation reaction, then the catalyst may comprise gallium and/or platinum catalyst. As described herein, a gallium and/or platinum catalyst comprises gallium, platinum, or both. The gallium and/or platinum catalyst may be carried by an alumina or alumina silica support, and may optionally comprise potassium. Such gallium and/or platinum catalysts are disclosed in U.S. Pat. No. 8,669,406, which is incorporated herein by reference in its entirety. However, it should be understood that other suitable catalysts may be utilized to perform the dehydrogenation reaction.

Figure 3:
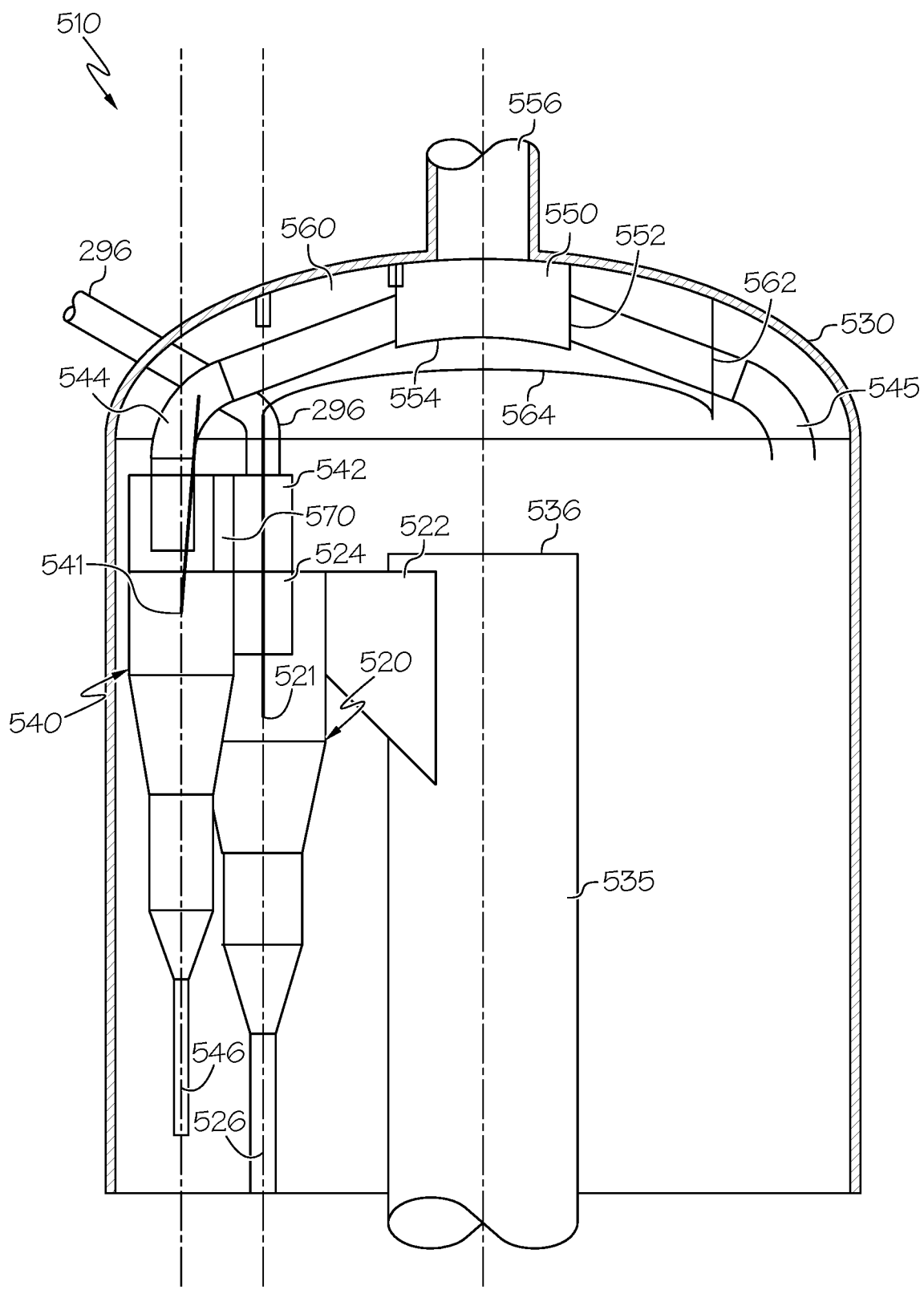
FIG. 3 schematically depicts a portion of a reaction system, according to one or more embodiments described herein.

FIG. 3 illustrates an embodiment of the upper portion of the reactor portion 200 of FIG. 2, referred to sometimes as the reactor vessel 510 wherein the separation device includes a primary separation device 520. The primary separation device 520 is contained within a shell 530 and has a body 521, an inlet 522, an outlet 524 and a solids discharge dipleg 526. A fluidized solid stream enters the primary separation device 520 through inlet 522. In the primary separation device 520, a major part of entrained solids, e.g. catalyst particles, are separated from the fluidized solid stream. The separated solids exit the primary separation device through discharge dipleg 526 leaving a primary separation device effluent which comprises solids not removed by the primary separation device 520 and fluid, e.g. gaseous product. The primary separation device effluent passes vertically upward and out of the primary separation device 520 through outlet 524 and into the secondary separation device 540 through primary separation device outlet tube 542 and then through crossover duct 570. The secondary separation device 540 further comprises a body 541, an outlet 544 and a solids discharge dipleg 546. The secondary separation device 540 further separates out solids from the primary separation device effluent. Solids separated out in the secondary separation device 540 exit downward through dipleg 546.

As depicted in FIG. 3, quench stream 296 may enter the upper portion of the primary separation device outlet tube 542, which is positioned directly above the primary separation device 520. It is believed that such an arrangement may be desirable for proper mixing of the quench stream with the effluent of the primary separation device 540 and to reduce residence time between the exit of the primary separation device 540 and the mixing with the quench stream 296.

Figure 4:
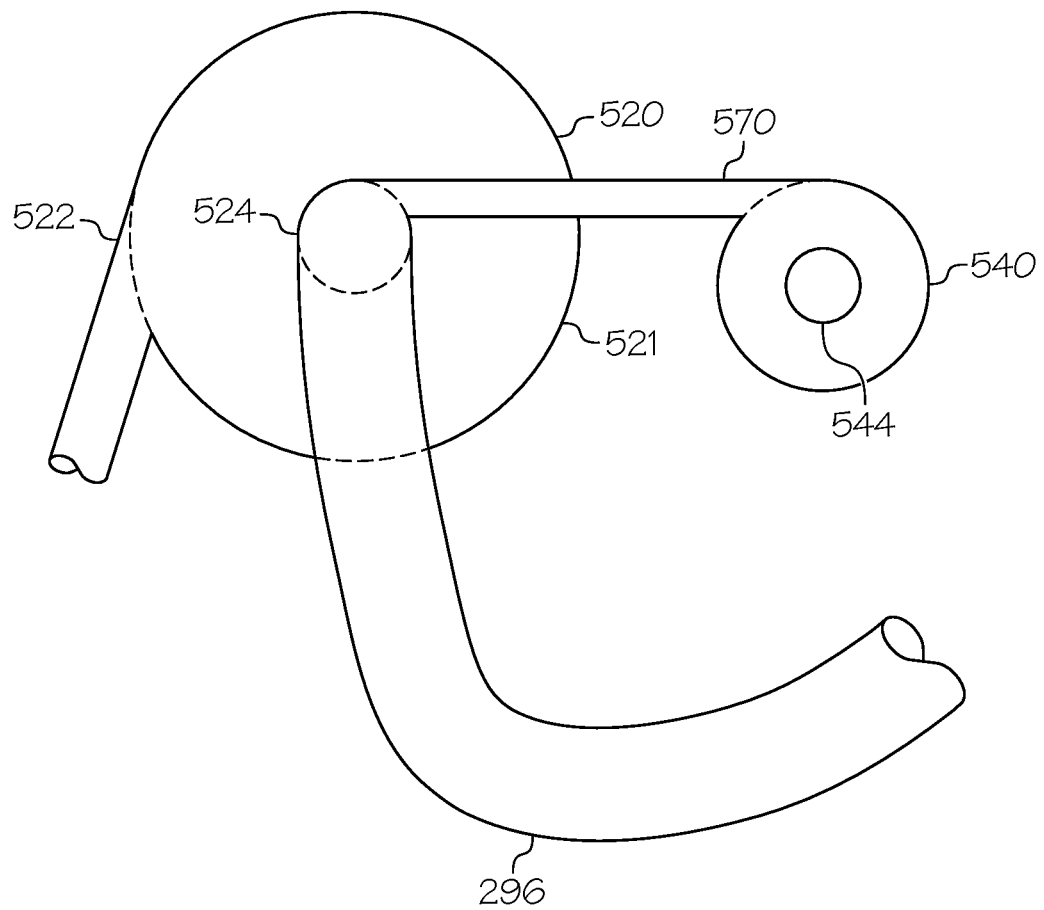
FIG. 4 schematically depicts a portion of a reaction system, according to one or more embodiments described herein.

Now referring to FIG. 4, an overhead view of one embodiment of the connection of the quench stream 296 to the primary separation device outlet tube 542 is depicted. The quench stream 296 may arrive via a pipe or other like conduit directly into the top of the primary separation device outlet tube 542 at a substantially vertical angle. The intermediate temperature dehydrogenation product may then pass through the crossover duct 570 to the secondary separation device 540.

Secondary separation device outlet 544 is fluidly connected to a second plenum 550. Second plenum 550 comprises a cylindrical skirt 552, a floor 554 and a second plenum outlet 556 which allows the secondary separation device effluent to pass from the second plenum and out of the vessel 510. As shown in FIG. 3, the second plenum is housed within a larger, higher volume first plenum 560. First plenum 560 comprises a skirt 562 and a floor 564. Primary separation device 520 may be supported by the first plenum 560.

Also shown in FIG. 3, the shell 530 further houses a riser 535. An unseparated stream of fluidized solid particles enters the shell through riser 535 which terminates in a plate 536. Riser 535 fluidly connects, i.e. allows passage of the fluidized solid particles, with the inlet 522 of the primary separation device 520 such that the unseparated stream of fluidized solid particles may pass from the riser 535 into primary separation device 520. If more than two separation stages are used, it is the effluent from the final separation stage which enters the second plenum. It will be understood that while FIG. 3 schematically illustrates only one primary separation device and one secondary separation device, additional primary and secondary separation devices may be placed around the periphery of the riser. For example, outlet tube 545 could be connected to another secondary separation device (not shown) which in turn is fed either by primary separation device 520 or by another primary separation device (not shown).

EXAMPLES

One or more examples are provided which may illustrate the various aspect of the present technology being disclosed.

Example 1

Modeling was used to determine the reduction in reaction rate of thermal cracking in various hydrocarbon feeds including propane, n-butane, ethane, and ethylbenzene. While it is appreciated that thermal cracking may also occur to the products of the chemical reaction, the thermal cracking of the unreacted portions of the stream provides a reasonable estimation for cracking of the whole stream and serves to simplify the model. The model also did not account for chemical equilibrium of thermally cracked products since the results would be negligible on the reaction rate of thermal cracking. It should be appreciated that the reduction in temperature of the product stream will reduce thermal cracking of both the product constituents and unreacted constituents in the stream. Power-law rate expressions from the open literature were used to estimate the rates of thermal cracking for the reactants. Specifically, reaction rate data for propane came from the Laidler coefficients described by Froment in "Buekens, A. G.; Froment, G. F. *Thermal Cracking of Propane*. I&EC Process Design and Development. Vol 7 No 3 (1968) 435-447." Reaction rate data for n-butane came from "Sagert, N. H.; Laidler, K. J. *Kinetics and Mechanisms of the Pyrolysis of n-Butane*. Canadian Journal of Chemistry. Vol 41 (1963) 838-847." Reaction rate data for ethane came from "Bartlit, J. R.; Bliss, H. *Kinetics of Ethane Pyrolysis*. AICHE Journal. Vol 11 No 3 (1965)." Reaction rate data for ethylbenzene came from "Domke, S. B.; Pogue, R. F.; Van Neer, F. J. R.; Smith, C. M.; Wojciechowski, B. W. *Investigation of the Kinetics of Ethylbenzene Pyrolysis Using a Temperature-Scanning Reactor*. Industrial & Engineering Chemistry Research. Vol 40 (2001) 5878-5884."

All rate expressions take the form:

$$r_i = k_i C_i^{n_i} \qquad \text{Equation 1}$$

where i is the reactant, $r_i$ is the reaction rate in gmol ft$^{-3}$ s$^{-1}$, $k_i$ is the rate constant, n is the order of reaction with respect to the reactant, and $C_i$ is the gas-phase concentration of the reactant in gmol ft$^{-3}$. The units for $k_i$ depend on the order of reaction. All rate expressions assume an Arrhenius form for the rate constant:

$$k_i = A_i \exp{\frac{-E_i}{RT}} \qquad \text{Equation 2}$$

where $A_i$ is the pre-exponential factor, $E_i$ is the activation energy in kcal gmol$^{-1}$, T is the absolute temperature in Kelvin, and R is the gas constant in kcal gmol$^{-1}$ K$^{-1}$. The units for $A_i$ depend on the order of reaction. Table 1 provides the literature values for the rate parameters described above for each reactant.

TABLE 1

Kinetic parameters for thermal cracking of propane, n-butane, ethane, and ethylbenzene.

| Parameter | Units | i = propane | i = n-butane | i = ethane | i = ethylbenzene |
|---|---|---|---|---|---|
| $n_i$ | — | 1.0 | 1.5 | 1.0 | 1.0 |
| $E_i$ | kcal gmol$^{-1}$ | 67.1 | 59.9 | 64.1 | 62.3 |
| $A_i$ | s$^{-1}$, or (ft$^3$)$^{1/2}$ gmol$^{-1/2}$ s$^{-1}$ | 2.58E+14 | 1.93E+13 | 3.16E+13 | 4.74E+13 |

The rates for thermal cracking are then estimated using Equations 1-2 at the target temperature and concentration of each reactant. (The reactant partial pressure is assumed to be 1.0 atmospheres (14.7 psi) in all cases.) Table 2 provides the results.

TABLE 2

Reaction rate at the target temperature and 1.0 atmospheres for each reactant.

| Description | Units | i = propane | i = n-butane | i = ethane | i = ethylbenzene |
|---|---|---|---|---|---|
| Target temperatures | ° C. | 620 | 600 | 750 | 595 |
| $r_i$ | gmol ft$^{-3}$ s$^{-1}$ | 3.8E-03 | 4.9E-03 | 2.2E-01 | 3.9E-03 |

Figure 5A:
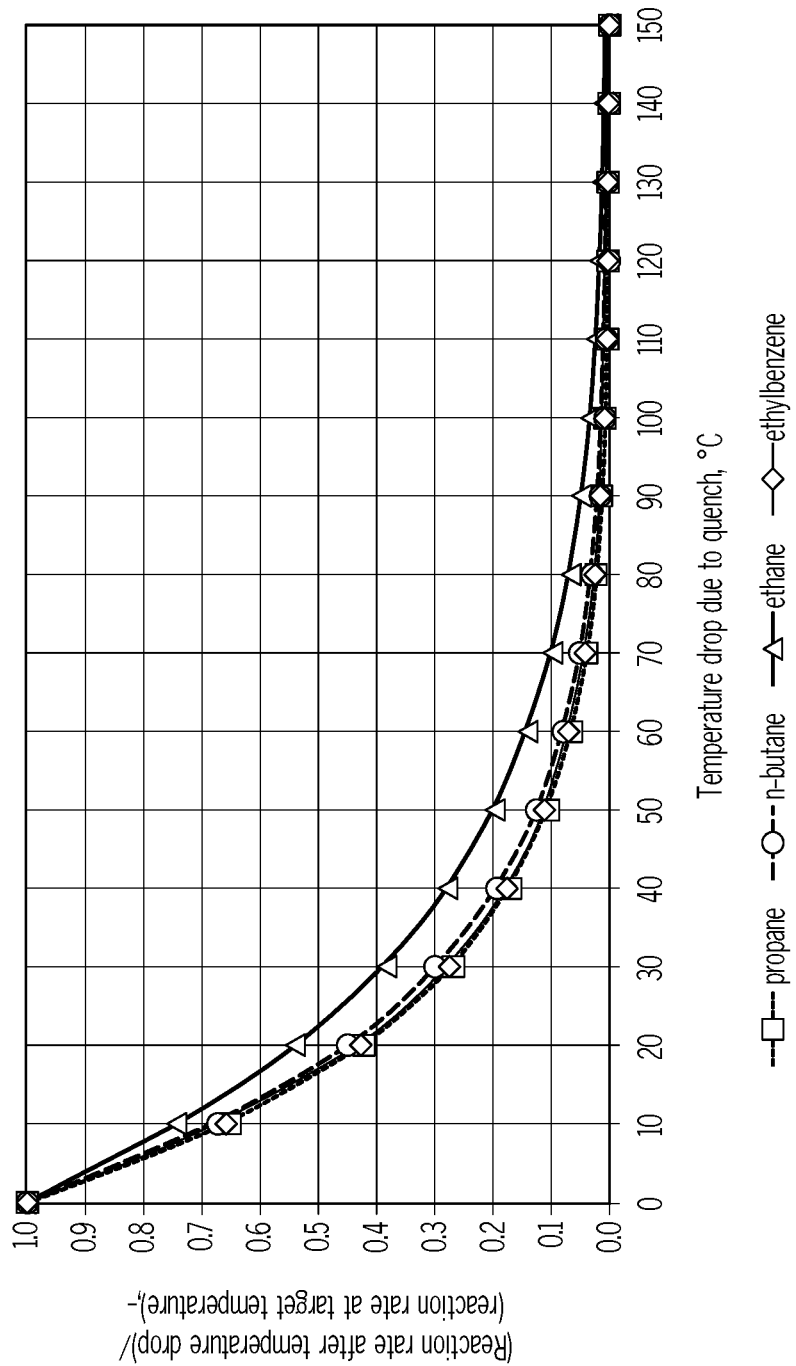
FIGS. 5A and 5B graphically depict the ratio of the reaction rate after temperature quench relative to the reaction rate before temperature quench (where the latter represents the rate at the respective target temperature for each reactant), according to one or more embodiments.
Figure 5B:
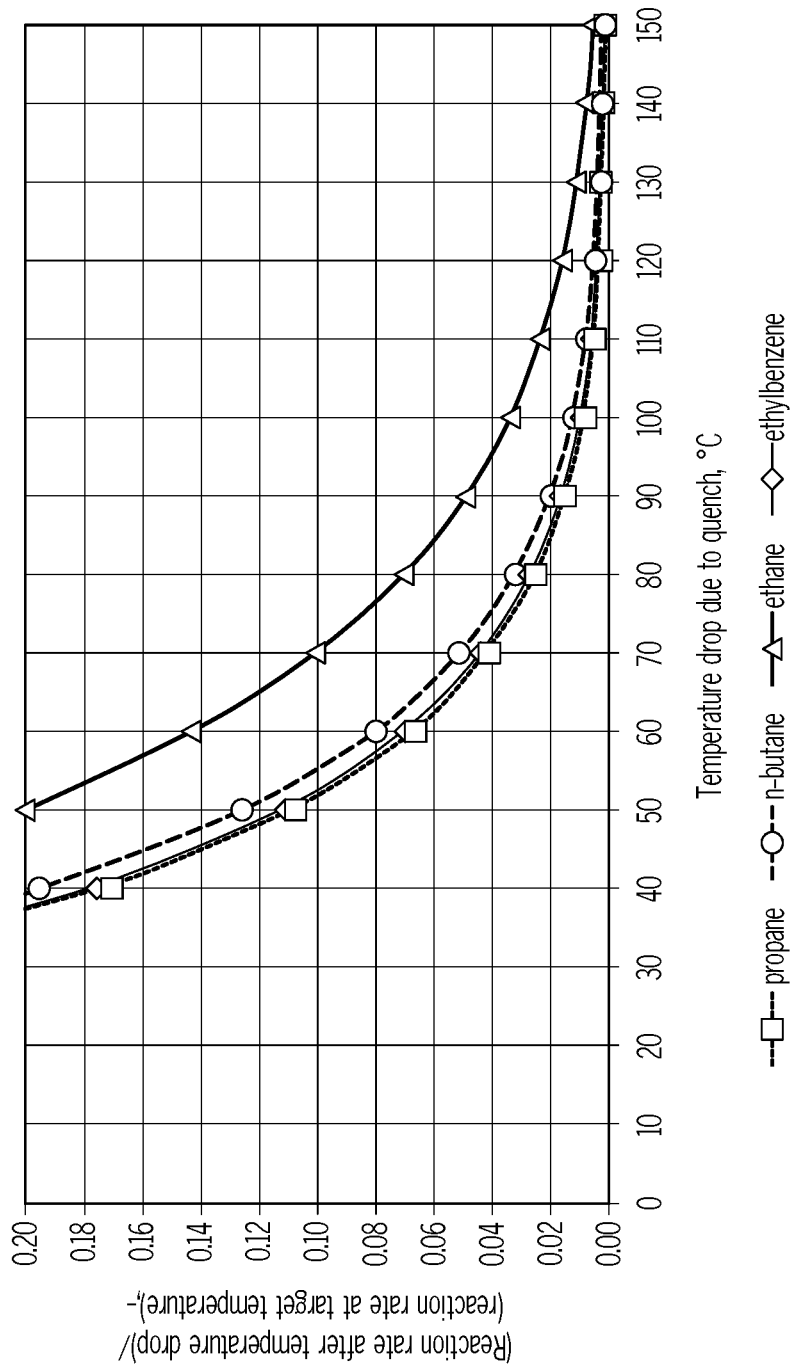

Finally, the rates for thermal cracking were estimated for cases where the temperature is reduced by 10° C. to 150° C. with respect to the target temperatures listed in Table 2. The results are shown in FIGS. 5A and 5B, which depict the same data but on different scales with respect to the y-axis. The results are presented as the ratio of the thermal cracking rate after temperature quench relative to the thermal cracking rate at the target temperature using the following equation:

$$\frac{r_i(\text{at } T_2)}{r_i(\text{at } T_1)} = \exp^{\frac{-E_i}{R}\left(\frac{1}{T_2} - \frac{1}{T_1}\right)} \qquad \text{Equation 3}$$

where $T_2$ is the temperature after quenching (e.g., described herein as the "intermediate temperature dehydrogenation product") and $T_1$ is the respective target temperature for the reactant (e.g., the temperature in the dehydrogenation reactor). Equation 3 is derived from Equations 1-2 and only requires knowledge of the activation energy. After a 10° C. temperature quench, the thermal cracking rate reduces by about 33-35% for propane, n-butane, and ethylbenzene, and about 27% for ethane. After a 20° C. temperature quench, the thermal cracking rate reduces by about 55-58% for propane, n-butane, and ethylbenzene, and about 47% for ethane. After a 30° C. temperature quench, the thermal cracking rate reduces by about 71-73% for propane, n-butane, and ethylbenzene, and about 61% for ethane.

Example 2

Figure 6:
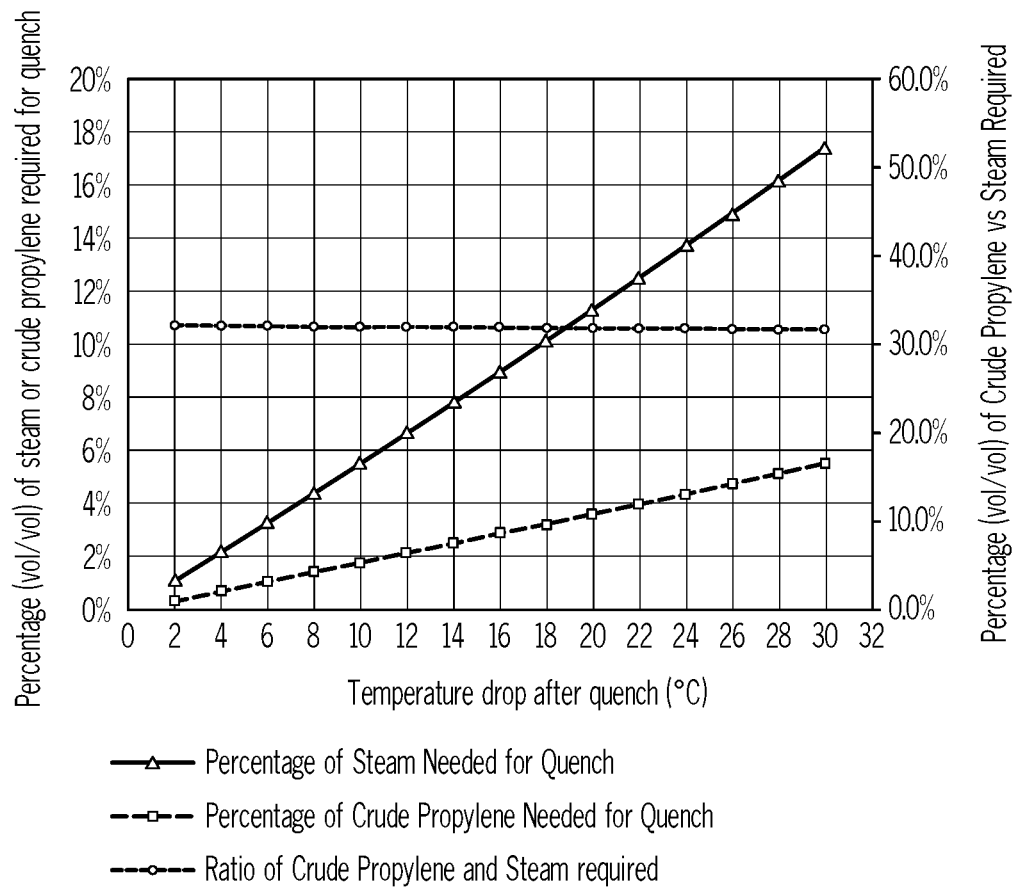
FIG. 6 graphically depicts the calculated percentages of steam and crude propylene relative to the product stream (vol/vol) needed in order to quench the product stream by various amounts, according to one or more embodiments.

The percentages of steam or crude propylene relative to the cracked gas product stream that is required to quench the product temperature by various degrees in the effluent of the primary separation device was calculated and is shown in FIG. 6, which shows the vol/vol percentage of steam or crude propylene needed for quenching a stream to a particular reduction in temperature. As can be seen in FIG. 6, the crude propylene for quenching is always approximately 32% of the steam required to quench for the same reduction in temperature. For example, to quench 10° C., 5.5% (vol/vol) of steam relative to the product stream exiting the primary separation device is required. As a comparison, only 1.77% (vol/vol) crude propylene relative to the product stream exiting the primary separation device is required. Less volume flow required for quenching by the crude propylene is an advantage when smaller equipment may be desired. In the calculations of Example 2, steam is assumed to be 178° C. and the recycled crude propylene is assumed to be 45° C. (the quench stream temperature). The temperature of the product stream before the quench (sometimes referred to as the "high temperature dehydrogenated product") is assumed to be 620° C.

Example 3

Figure 7:
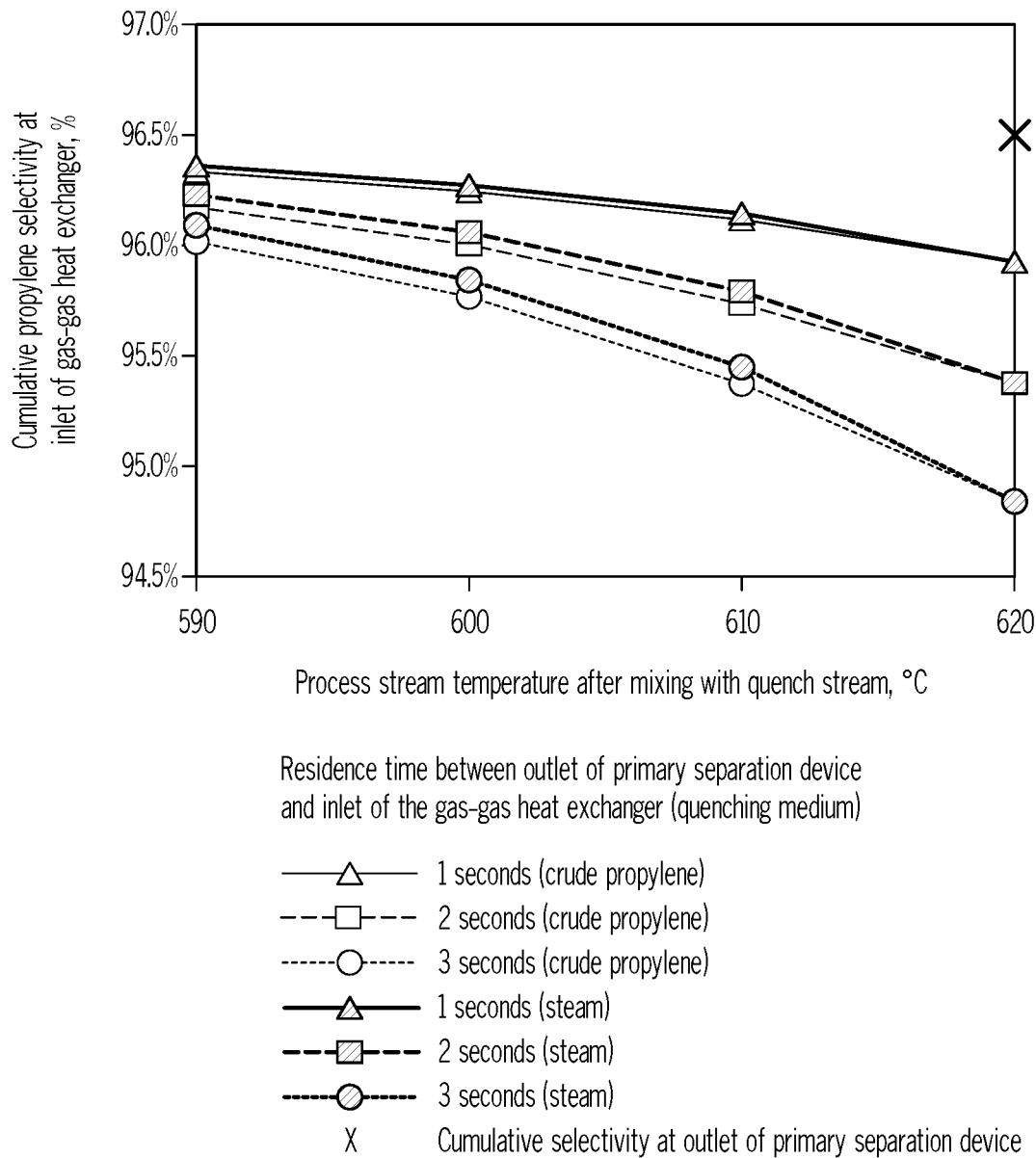
FIG. 7 graphically depicts the calculated cumulative propylene selectivity (%) as a function of temperature drop after mixing with the quench stream, quenching medium (steam or crude propylene), and residence time between the outlet of the primary separation devices and inlet of the gas-gas heat exchanger, according to one or more embodiments.

Modeling was utilized to illustrate the propylene selectivity and conversion achieved with embodiments of the present application. For reaction of propane to propylene, the cumulative selectivity toward propylene as a function of post-quench residence time, quenching medium, and temperature drop was calculated and is shown in FIG. 7. It shows that without quenching the process stream, and with a residence time between the outlet of the primary separation device and the inlet of a gas-gas heat exchanger on the order of seconds or more, the thermal (non-catalytic) reactions will lower the cumulative selectivity toward propylene. For example, if the process stream exits the primary separation device without being quenched and has a residence time of 3 seconds before reaching the gas-gas heat exchanger, the cumulative selectivity toward propylene decreases by about 1.7%, and the decrease in cumulative selectivity changes to about 1.1% after quenching by 10° C. and to about 0.7% after quenching by 20° C. It should be noted that for the same temperature drop, the case where steam was used as the quenching medium has a selectivity benefit compared with the case where crude propylene is used as the quenching medium because steam will lower the partial pressure of hydrocarbons and therefore reduce the driving force for further thermal cracking reactions. However, this additional benefit from steam dilution is minor when compared with the benefit from the temperature change.

The following assumptions were made for the process stream at the outlet of the primary separation device: the cumulative propylene selectivity is 96.5%, the propane conversion is 46.4%, the temperature is 620° C., and the pressure is 19 psia. The quench and product streams are assumed to mix instantaneously, and the resulting stream is assumed to remain isothermal with negligible pressure drop up to the gas-gas exchanger. Only thermal (non-catalytic) reactions are assumed to occur between the outlet of the primary separation device and the inlet of the gas-gas exchanger, because the majority of catalyst is separated in the primary separation device. The thermal reaction rate is taken on the unreacted propane that is available using the power-law expression and coefficients corresponding to propane from Example 1 (with the same assumptions regarding thermal cracking of the dehydrogenated product, propylene). FIG. 6 from Example 2 can be referenced to determine the amount of steam or crude propylene needed for quench.

Figure 8:
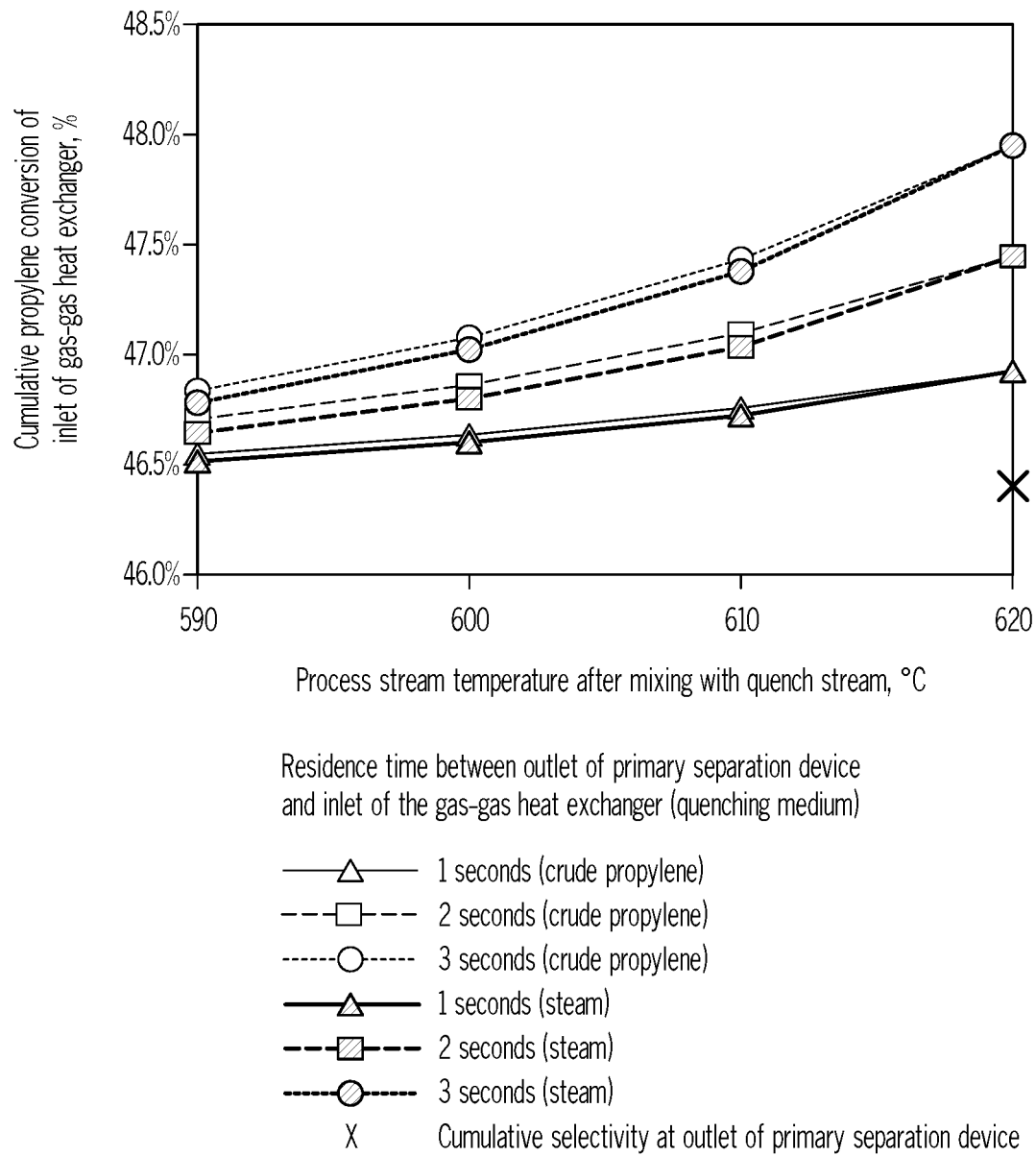
FIG. 8 graphically depicts the calculated cumulative propane conversion (%) as a function of temperature drop after mixing with the quench stream, quenching medium (steam or crude propylene), and residence time between the outlet of the primary separation device and inlet of the gas-gas heat exchanger, according to one or more embodiments.

Additionally, using similar methodology, FIG. 8 depicts propane conversion at the entrance of the heat exchanger. As shown in FIG. 8, greater process stream temperatures following quenching (i.e., "intermediate temperature dehydrogenation product") corresponded to greater conversion of propane due to thermal cracking.

For the purposes of describing and defining the present invention it is noted that the term "about" is utilized herein to represent the inherent degree of uncertainty that may be attributed to any quantitative comparison, value, measurement, or other representation. The term is also utilized herein to represent the degree by which a quantitative representation may vary from a stated reference without resulting in a change in the basic function of the subject matter at issue.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Generally, "inlet ports" and "outlet ports" of any system unit of the reactor system 102 described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the reactor system 102 to which a pipe, conduit, tube, hose, material transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

In a first aspect of the present disclosure, a method for forming light olefins may include introducing a hydrocarbon feed stream into a reactor, reacting the hydrocarbon feed stream with a dehydrogenation catalyst in the reactor to form a high temperature dehydrogenated product, separating at least a portion of the dehydrogenation catalyst from the high temperature dehydrogenated product in a primary separation device, combining the high temperature dehydrogenation product with a quench stream to cool the high temperature dehydrogenation product and form an intermediate temperature dehydrogenation product following the exit of high temperature dehydrogenation product from the primary separation device, and cooling the intermediate temperature dehydrogenation product to form a cooled dehydrogenation product. The dehydrogenated product may include at least a portion of the hydrocarbon feed stream that was not catalytically reacted. The temperature of the dehydrogenated product and dehydrogenation catalyst in the primary separation device may be at least 550° C. The quench stream may be a gas stream. The temperature of the intermediate temperature dehydrogenation product may be at least 10° C. less than the temperature of the high temperature dehydrogenation product. A portion of the cooled dehydrogenation product may be utilized as at least a portion of the quench stream.

A second aspect of the present disclosure may include the first aspect where the hydrocarbon feed may include propane, n-butane, iso-butane, ethane, ethylbenzene, or combinations thereof.

A third aspect of the present disclosure may include either of the first or second aspects where the quench stream may be at least 300° C. less than the temperature of the high temperature dehydrogenated product.

A fourth aspect of the present disclosure may include any of the first through third aspects where the rate of thermal cracking in the intermediate temperature dehydrogenation product of the portion of the hydrocarbon feed stream that was not catalytically reacted may be less than 90% of that in the high temperature dehydrogenated product.

A fifth aspect of the present disclosure may include any of the first through fourth aspects further including passing the intermediate temperature product to a secondary separation device where the remainder of the dehydrogenation catalyst may be removed from the intermediate temperature product.

A sixth aspect of the present disclosure may include any of the first through fifth aspects where the cooled dehydrogenation product may have a temperature of less than or equal to 150° C.

A seventh aspect of the present disclosure may include any of the first through sixth aspects where a heat exchanger and/or liquid quenching system may cool the intermediate temperature dehydrogenation product to the cooled dehydrogenation product.

An eighth aspect of the present disclosure may include any of the first through seventh aspects where the quench stream may comprise less than 3 wt. % steam.

A ninth aspect of the present disclosure may include any of the first through eighth aspects where the dehydrogenation catalyst may be a solid and the high temperature dehydrogenated product may be a gas.

A tenth aspect of the present disclosure may include any of the first through ninth aspects where the quench stream may include one or more of ethylene, propylene, or a butene isomer.

An eleventh aspect of the present disclosure may include any of the first through tenth aspects where the dehydrogenation catalyst may be a gallium and/or platinum catalyst.

In a twelfth aspect of the present disclosure, a method for forming light olefins may include introducing a hydrocarbon feed stream into a reactor, reacting the hydrocarbon feed stream with a dehydrogenation catalyst in the reactor to form a high temperature dehydrogenated product, separating at least a portion of the dehydrogenation catalyst from the high temperature dehydrogenated product in a primary separation device, combining the high temperature dehydrogenation product with a quench stream to cool the high temperature dehydrogenation product and form an intermediate temperature dehydrogenation product following the exit of high temperature dehydrogenation product from the primary separation device, passing the intermediate temperature product to a secondary separation device where the remainder of the dehydrogenation catalyst is removed from the intermediate temperature product, and cooling the intermediate temperature dehydrogenation product to form a cooled dehydrogenation product. The dehydrogenated product may include at least a portion of the hydrocarbon feed stream that was not catalytically reacted. The temperature of the dehydrogenated product and dehydrogenation catalyst in the primary separation device may be at least 550° C. The quench stream may be a gas stream. The temperature of the intermediate temperature dehydrogenation product may be at least 10° C. less than the temperature of the high temperature dehydrogenation product. A portion of the cooled dehydrogenation product may be utilized as at least a portion of the quench stream.

A thirteenth aspect of the present disclosure may include the twelfth aspect where the hydrocarbon feed may include propane, n-butane, iso-butane, ethane, ethylbenzene, or combinations thereof.

A fourteenth aspect of the present disclosure may include either of the twelfth or thirteenth aspects where the rate of thermal cracking in the intermediate temperature dehydrogenation product of the portion of the hydrocarbon feed stream that was not catalytically reacted may be less than 70% of that in the high temperature dehydrogenated product.

A fifteenth aspect of the present disclosure may include any of the twelfth through fourteenth aspects where the cooled dehydrogenation product may have a temperature of less than or equal to 150° C.

The invention claimed is:

1. A method comprising:
   introducing a hydrocarbon feed stream into a reactor, wherein the reactor comprises at least one reactor section operating as a fast fluidized, turbulent, or bubbling bed upflow reactor or a dilute phase riser reactor;
   reacting the hydrocarbon feed stream with a dehydrogenation catalyst in the reactor to form a high temperature dehydrogenated product having a temperature of at least 550° C., the dehydrogenated product comprising at least a portion of the hydrocarbon feed stream that was not catalytically reacted;
   separating at least a portion of the dehydrogenation catalyst from the high temperature dehydrogenated product in a primary separation device, wherein the temperature of the dehydrogenated product and dehydrogenation catalyst in the primary separation device is at least 550° C.;

following the exit of a high temperature dehydrogenation product from the primary separation device, combining the high temperature dehydrogenation product with a quench stream to cool the high temperature dehydrogenation product and form an intermediate temperature dehydrogenation product, and wherein a temperature of the intermediate temperature dehydrogenation product is at least 10° C. less than a temperature of the high temperature dehydrogenation product, and wherein the temperature of the high temperature dehydrogenation product is about equivalent to the temperature of the high temperature dehydrogenated product; and cooling the intermediate temperature dehydrogenation product to form a cooled dehydrogenation product, wherein a portion of the cooled dehydrogenation product is utilized as at least a portion of the quench stream.

2. The method of claim 1, wherein the hydrocarbon feed comprises propane, n-butane, iso-butane, ethane, ethylbenzene, or a combination thereof.

3. The method of claim 1, wherein the quench stream is at least 300° C. less than the temperature of the high temperature dehydrogenated product.

4. The method of claim 1, wherein the rate of thermal cracking in the intermediate temperature dehydrogenation product of the portion of the hydrocarbon feed stream that was not catalytically reacted is less than 90% of that in the high temperature dehydrogenated product.

5. The method of claim 1, further comprising passing the intermediate temperature dehydrogenation product to a secondary separation device where the remainder of the dehydrogenation catalyst is removed from the intermediate temperature dehydrogenation product.

6. The method of claim 1, wherein the cooled dehydrogenation product has a temperature of less than or equal to 150° C.

7. The method of claim 1, wherein a heat exchanger and/or liquid quenching system cools the intermediate temperature dehydrogenation product to the cooled dehydrogenation product.

8. The method of claim 1, wherein one or more of:
the quench stream comprises less than 3 wt. % steam; or
the quench stream comprises one or more of ethylene, propylene, or a butene isomer.

9. The method of claim 1, wherein the dehydrogenation catalyst is a solid and the high temperature dehydrogenated product is a gas.

10. The method of claim 1, wherein the quench stream is a gas stream.

11. The method of claim 1, wherein the dehydrogenation catalyst is a gallium and/or platinum catalyst.

12. The method of claim 1, wherein the reactor comprises an upstream reactor section and a downstream reactor section and the upstream reactor section operates as the fast fluidized, turbulent, or bubbling bed upflow reactor.

13. The method of claim 12, wherein the downstream reactor section operates as the dilute phase riser reactor.

14. A method comprising:
introducing a hydrocarbon feed stream into a reactor, wherein the reactor comprises at least one reactor section operating as a fast fluidized, turbulent, or bubbling bed upflow reactor or a dilute phase riser reactor;

reacting the hydrocarbon feed stream with a dehydrogenation catalyst in the reactor to form a high temperature dehydrogenated product having a temperature of at least 550° C., the dehydrogenated product comprising at least a portion of the hydrocarbon feed stream that was not catalytically reacted;

separating at least a portion of the dehydrogenation catalyst from the high temperature dehydrogenated product in a primary separation device, wherein the temperature of the dehydrogenated product and dehydrogenation catalyst in the primary separation device is at least 550° C.;

following the exit of a high temperature dehydrogenation product from the primary separation device, combining the high temperature dehydrogenation product with a quench stream to cool the high temperature dehydrogenation product and form an intermediate temperature dehydrogenation product, wherein a temperature of the intermediate temperature dehydrogenation product is at least 10° C. less than a temperature of the high temperature dehydrogenation product, and wherein the temperature of the high temperature dehydrogenation product is about equivalent to the temperature of the high temperature dehydrogenated product;

passing the intermediate temperature dehydrogenation product to a secondary separation device where the remainder of the dehydrogenation catalyst is removed from the intermediate temperature dehydrogenation product; and cooling the intermediate temperature dehydrogenation product to form a cooled dehydrogenation product, wherein a portion of the cooled dehydrogenation product is utilized as at least a portion of the quench stream.

15. The method of claim 14, wherein the hydrocarbon feed comprises propane, n-butane, iso-butane, ethane, ethylbenzene, or a combination thereof.

16. The method of claim 14, wherein the rate of thermal cracking in the intermediate temperature dehydrogenation product of the portion of the hydrocarbon feed stream that was not catalytically reacted is less than 70% of that in the high temperature dehydrogenated product.

17. The method of claim 14, wherein the quench stream is a gas stream.

18. The method of claim 14, wherein the reactor comprises an upstream reactor section and a downstream reactor section and the upstream reactor section operates as the fast fluidized, turbulent, or bubbling bed upflow reactor.

19. The method of claim 18, wherein the downstream reactor section operates as the dilute phase riser reactor.

* * * * *